United States Patent
Alvi et al.

(10) Patent No.: US 8,602,574 B1
(45) Date of Patent: Dec. 10, 2013

(54) SELF-INSPECTION APPARATUS

(75) Inventors: Haroon I. Alvi, Southlake, TX (US); Nancy L. Cozzie, Southlake, TX (US); Michael R. Wilkinson, Richardson, TX (US); Arnold Ochoa, Garland, TX (US); Brian Eaton, Plano, TX (US)

(73) Assignee: NIH Enterprises, Inc., Southlake, TX (US)

( * ) Notice: Subject to any disclaimer, the term of this patent is extended or adjusted under 35 U.S.C. 154(b) by 0 days.

(21) Appl. No.: 13/118,752

(22) Filed: May 31, 2011

(51) Int. Cl.
  *G02B 7/182* (2006.01)

(52) U.S. Cl.
  USPC .......................................... 359/872

(58) Field of Classification Search
  USPC ........................................ 359/838, 872, 881
  See application file for complete search history.

(56) References Cited

U.S. PATENT DOCUMENTS

| | | | |
|---|---|---|---|
| 1,387,415 A * | 8/1921 | Lee | 248/126 |
| 1,389,053 A * | 8/1921 | King | 359/879 |
| 1,522,412 A * | 1/1925 | Bordignone | 248/480 |
| 1,905,623 A * | 4/1933 | Deitz | 248/487 |
| 2,013,882 A * | 9/1935 | Francis | 248/277.1 |
| 2,750,840 A * | 6/1956 | Sklarek | 248/481 |
| 3,236,152 A * | 2/1966 | Alford | 248/481 |
| 3,411,842 A * | 11/1968 | Levy | 359/879 |
| 3,989,359 A | 11/1976 | Shutt | |
| 4,257,680 A | 3/1981 | Baczkowski | |
| 4,623,955 A * | 11/1986 | Santini | 362/135 |
| 4,702,572 A * | 10/1987 | Cossey | 359/876 |
| 4,730,913 A * | 3/1988 | Boothe | 359/881 |
| 5,027,472 A * | 7/1991 | Goodman | 16/422 |
| 5,301,068 A | 4/1994 | Minisci | |
| 5,311,366 A | 5/1994 | Gerace | |
| D350,599 S * | 9/1994 | Silverstein et al. | D23/309 |
| 5,354,026 A * | 10/1994 | Bulla | 248/227.1 |
| D361,626 S * | 8/1995 | Brown | D23/309 |
| 5,601,537 A | 2/1997 | Frassica | |
| 5,653,700 A | 8/1997 | Byrne et al. | |
| 5,825,564 A * | 10/1998 | Mazarac | 359/872 |
| 6,273,575 B1 | 8/2001 | Downs et al. | |
| 6,370,741 B1 * | 4/2002 | Lu | 24/523 |
| 6,544,240 B1 | 4/2003 | Borodulin et al. | |
| 6,691,330 B2 * | 2/2004 | Baker | 4/246.1 |
| 6,926,708 B1 | 8/2005 | Franks-Farah et al. | |
| 7,445,189 B2 * | 11/2008 | Cox et al. | 248/415 |
| 7,552,485 B1 * | 6/2009 | Harrison, Jr. | 4/246.1 |
| 2009/0145938 A1 * | 6/2009 | Kahn | 224/183 |
| 2011/0083264 A1 * | 4/2011 | Gunderson | 4/661 |

FOREIGN PATENT DOCUMENTS

| | | | | |
|---|---|---|---|---|
| JP | 04106235 A * | 4/1992 | | E03D 9/00 |
| JP | 06167042 A * | 6/1994 | | E03D 11/02 |
| JP | 11107352 A * | 4/1999 | | E03D 11/02 |
| JP | 2000080699 A * | 3/2000 | | E03D 9/00 |

* cited by examiner

*Primary Examiner* — Frank Font

(57) ABSTRACT

A self-inspection apparatus comprising a mirror support member having a hinge proximate an end thereof and configured to couple to a toilet bowl rim or a toilet seat, and a mirror coupled to the mirror support member at the hinge and configured to be positionable for self-inspection. A method of manufacturing a self-inspection apparatus is also provided.

15 Claims, 3 Drawing Sheets

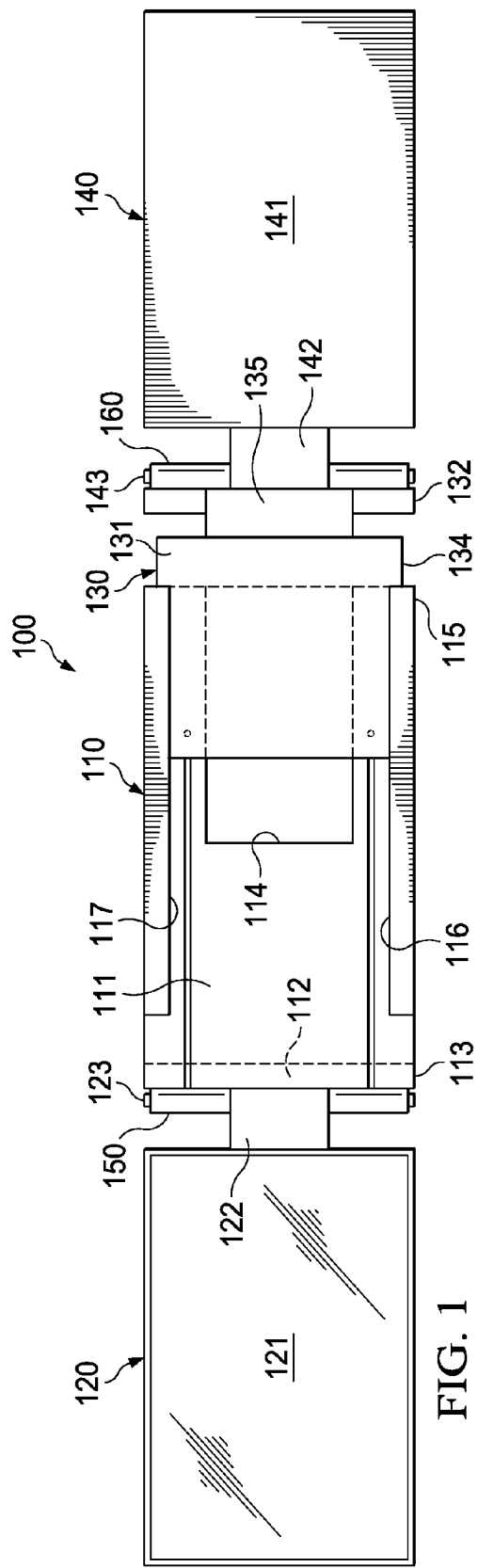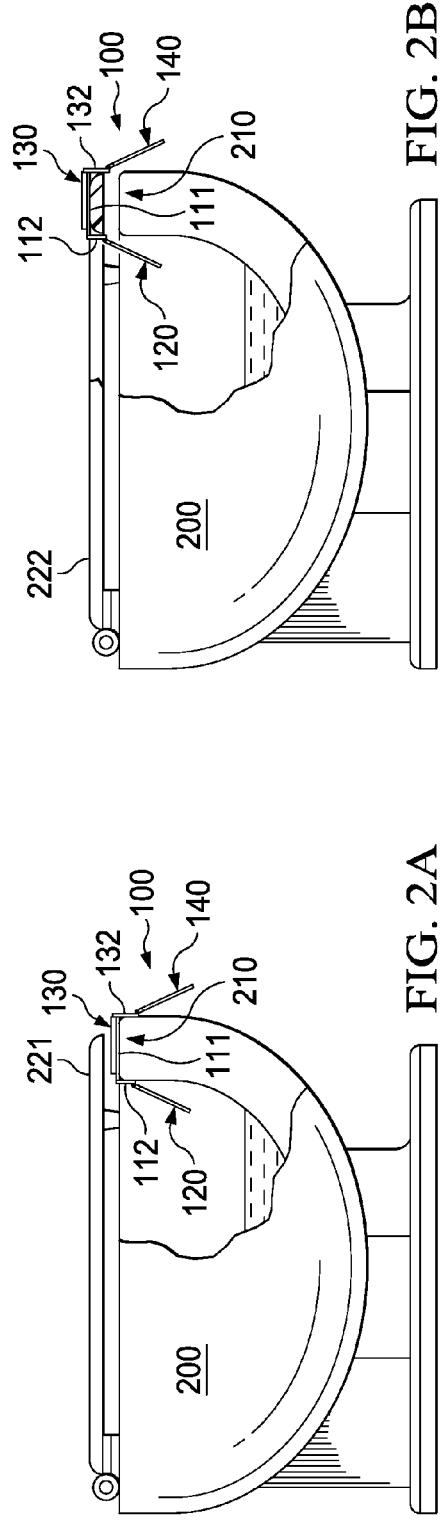

SELF-INSPECTION APPARATUS

TECHNICAL FIELD

This application is directed, in general, to an apparatus for self-inspection of the genital region.

BACKGROUND

Inability of the bladder to function normally in a patient can involve problems of urinary retention. This dysfunction can result from a number of different causes, such as extensive abdominal surgical operations, infection, various diseases, etc. If the sphincter muscle is too tight or the bladder muscles are too lax the patient may be able to urinate but may be unable to completely empty the bladder during urination.

Patients with urinary retention, as well as other issues, require catheterization to enable the bladder to be satisfactorily emptied. In some cases a urine collection bag and an indwelling urethral catheter are used, the catheter forming a passageway from the bladder to the externally-carried collection bag which can regularly be emptied. This arrangement, however, is cumbersome and moreover leaves the patient at increased risk of infection, bacteria being able to grow and track along the catheter from the collection bag or around the catheter along the urethra.

The alternative and more acceptable solution is the insertion of a transient urethral catheter to allow the patient to void in the bathroom when appropriate or on a predetermined time schedule, such as every three to four hours. For women, this intermittent self-catheterization can be very difficult to carry out, since the patient must be able to locate the urinary meatus accurately in order to insert the catheter into the urethra.

SUMMARY

One aspect provides a self-inspection apparatus comprising a mirror support member having a hinge proximate an end thereof and configured to couple to a toilet bowl rim or a toilet seat, and a mirror coupled to the mirror support member at the hinge and configured to be positionable for self-inspection. A method of manufacturing a self-inspection apparatus is also provided.

BRIEF DESCRIPTION

Reference is now made to the following descriptions taken in conjunction with the accompanying drawings, in which:

FIG. 1 is an expanded plan view of one embodiment of a self-inspection apparatus 100 constructed in accordance with the principles of the present disclosure;

FIG. 2A is a side elevation views of the self-inspection apparatus 100 of FIG. 1 in relation to a partial sectional view of a toilet bowl rim 210;

FIG. 2B is a side elevation views of the self-inspection apparatus 100 of FIG. 1 in relation to a partial sectional view of a toilet seat 222;

Figure 5:
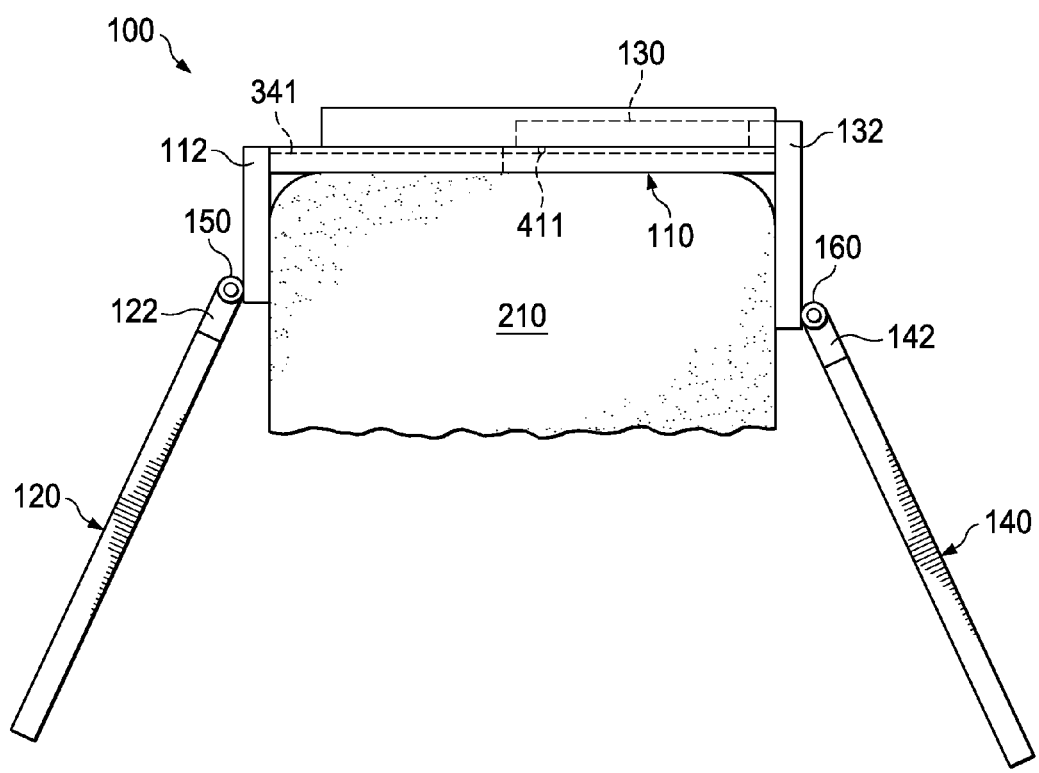
Figure 6:
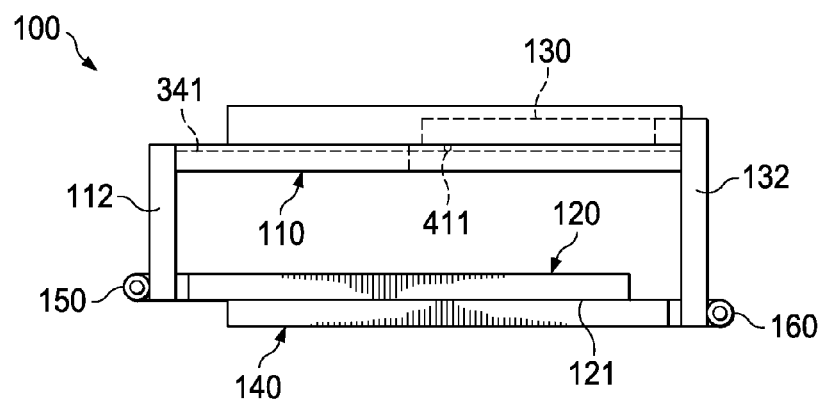

FIG. 5 is a side elevation view of the self-inspection apparatus 100 of FIG. 1 as it sits atop the toilet bowl rim 210; and FIG. 6 is a side elevation view of the self-inspection apparatus 100 folded for transport or storage.

DETAILED DESCRIPTION

Referring now to FIG. 1, illustrated is an expanded plan view of one embodiment of a self-inspection apparatus 100 constructed in accordance with the principles of the present disclosure. The self-inspection apparatus 100 of the embodiment of FIG. 1 comprises a mirror support member 110, a mirror member 120, a counterweight support member 130, a counterweight 140, and first and second hinges 150, 160, respectively.

The mirror support member 110, in one embodiment, has a horizontal portion 111, a mirror support member hinge portion 112 that is substantially normal to the horizontal portion 111 at an end 113 of the mirror support member 110, a void 114 proximate an opposite end 115 and first and second opposing channels 116, 117. The mirror member 120, in one embodiment, may have a mirror portion 121 and a mirror hinge portion 122. The mirror hinge portion 122 may be coupled to the mirror support member hinge portion 112 with a first hinge pin 123. Alternative configuration may also coupled the mirror support member hinge portion 112 with the first hinge pin 123. The first hinge 150, for example, may comprise a mirror support member hinge portion 112, the mirror hinge portion 122, and the first hinge pin 123. The mirror support member hinge portion 112 of the first hinge 150 may be formed integral to the horizontal portion 111 of the mirror support member 110. The mirror hinge portion 122 of the first hinge 150 may be formed integral to the mirror member 120. In one embodiment, the first hinge 150 is a friction-fit hinge wherein the mirror support member hinge portion 112 and the mirror hinge portion 122 are formed from a durable rigid plastic. While the hinge described above is that of a flat hinge having a central pin joining two substantially-flat parts, other articulating mechanisms (e.g., hinges) such as a ball and socket, swivel, universal joint, etc., may also be employed. In one embodiment, the mirror 125 may be applied as a mirror-like foil to one face of the mirror member 120 or the mirror member 120 may be formed around a preformed mirror. The self-inspection apparatus 100 may be cleaned with common household disinfectant cleaner.

The counterweight support member 130, in one embodiment, may have a horizontal portion 131, a counterweight support member hinge portion 132 that is substantially normal to the horizontal portion 131 at an end 134 of the counterweight support member 130, and a tongue 135. The counterweight 140 may also have a body portion 141 and a counterweight hinge portion 142. The counterweight hinge portion 142 may be coupled to the counterweight support member hinge portion 132 with a second hinge pin 143. For example, the second hinge 160 may comprise the counterweight support member hinge portion 132, the counterweight hinge portion 142, and the second hinge pin 143. The counterweight support member hinge portion 132 of the second hinge 160 may be formed integral to the horizontal portion 131 of the counterweight support member 130. The counterweight hinge portion 142 of the second hinge 160 may, likewise, be formed integral to the counterweight 140. In one embodiment, the second hinge 160 is also a friction-fit hinge wherein the counterweight support member hinge portion 132 and the counterweight hinge portion 142 are formed from the same durable rigid plastic as the mirror support member 110. Nonetheless, other embodiments exist wherein the other hinges described above are employed.

The mirror member 120 and the counterweight 140 are, in one embodiment, substantially equal in weight. In one embodiment, both the first and second hinges 150, 160, respectively, are friction-fit hinges. Therefore, in this embodiment, the combination of substantially equal weight of the mirror member 120 and the counterweight 140 together with friction-fit hinges 150, 160 allows the mirror member 120 to be placed at whatever is a convenient angle for self-inspection and the angle is easily matched for the counterweight 140 so that the self-inspection apparatus 100 remains balanced and stable when positioned on a toilet rim or a toilet seat.

The self-inspection apparatus 100 is configured to selectively rest upon either a toilet bowl rim with a split toilet seat or on a toilet seat for a toilet bowl equipped with a continuous toilet seat. To the extent that other seat and/or bowl configurations exist or are developed in the future, the self-inspection apparatus 100 of FIG. 1 would be equally applicable.

Referring now to FIGS. 2A and 2B, illustrated are side elevation views of the self-inspection apparatus 100 of FIG. 1 in relation to a partial sectional view of a toilet bowl rim 210 (FIG. 2A) and to a toilet seat 222 (FIG. 2B). The self-inspection apparatus 100, in these embodiments, is positioned at the frontmost portion of a toilet bowl 200, either on the toilet rim 210 in the case of a split toilet seat 221, or on the toilet seat 222 itself in the case of a continuous toilet seat 222 as the situation may require. In these embodiments, the horizontal portion 111 of the mirror support member 110 may be placed on the rim 210 or the toilet seat 222, as applicable, with the mirror support member hinge portion 112 abutting the rim 210 or the seat 222, as applicable. The counterweight support member 130 may then be slid with respect to the mirror support member 110 until the counterweight support member hinge portion 132 contacts the other side of the rim 210 or the seat 222. During this sliding, the tongue 135 in this embodiment travels a distance in the void 114 from the vicinity of the opposite end 115 toward the other end 113 as the counterweight support member 130 slides between the first and second opposing channels 116, 117. The self-inspection apparatus 100 can accommodate toilet bowls/seats with rim thicknesses from about 1⅜" to about 4", among other thicknesses. The 4" capability will accommodate virtually all continuous toilet seats. While the preceding description has depicted a preferred embodiment, other methods of temporarily fastening the mirror support member to the bowl rim or seat may be used, such as: double sided tape, suction cups, etc.

It is apparent from the embodiment of FIGS. 2A and 2B that the apparatus 100 may be configured to have its mirror portion rest within a footprint of the toilet bowl rim 210. This aspect of the apparatus 100, when applicable, allows the user of the apparatus 100 to insert a catheter with reduced likelihood that urine will escape the confines of the toilet 200. Were the mirror portion of the apparatus 100 to rest outside of the footprint of the toilet bowl rim 210, the likelihood that urine will escape the confines of the toilet 200 is greatly increased. Accordingly, when the mirror portion of the apparatus 100 is placed within the footprint of the toilet bowl rim 210, and particularly on the frontmost portion thereof, the user of the apparatus 100 would likely sit on the toilet in a manner similar to if he or she were urinating, and while in this position, insert the catheter.

Figure 3A:
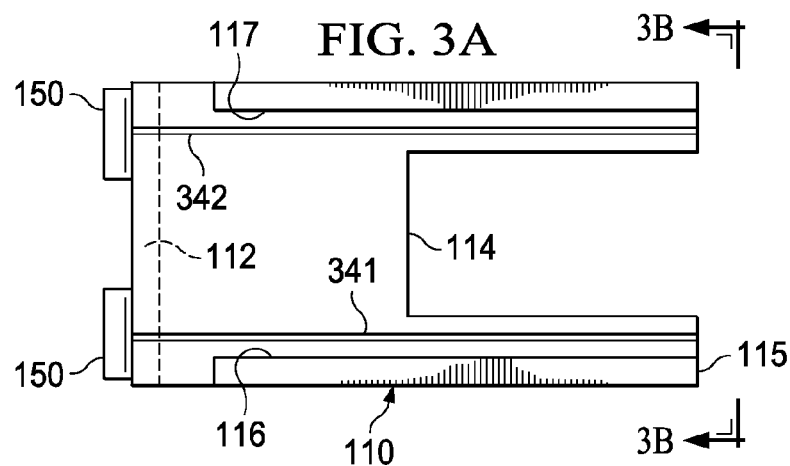
FIG. 3A is a plan view of the mirror support member 110 of FIG. 1.
Figure 3B:
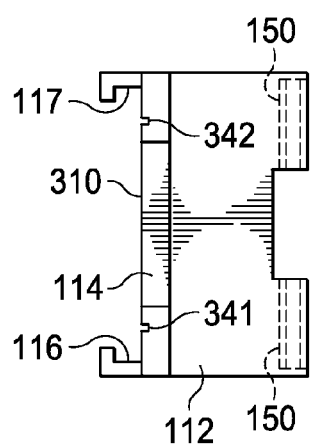
FIG. 3B is an end view of the mirror support member 110 of FIG. 1.

Referring now to FIGS. 3A and 3B, illustrated are plan and end views, respectively, of the mirror support member 110 of FIG. 1. The end view FIG. 3B is as viewed from plane 3B-3B. The first and second opposing channels 116, 117, respectively, extend upwardly from the upper surface 310, and the mirror support member 110 further comprises first and second tracks 341, 342, respectively, on the upper surface 310. A portion of the first hinge 150 is located at a lower end of the mirror support member hinge portion 112.

Figure 4:
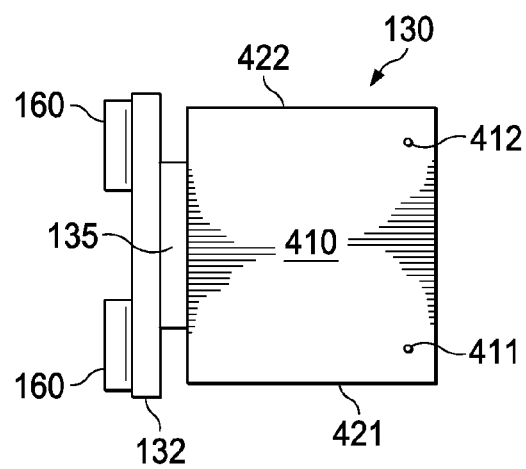
FIG. 4 is a plan view of an under surface 410 of the counterweight support member 130 of FIG. 1.

Referring now to FIG. 4 with continuing reference to FIG. 3B, illustrated is a plan view of an under surface 410 of the counterweight support member 130 of the embodiment of FIG. 1. The counterweight support member 130 further comprises first and second protuberances 411, 412, respectively, on the under surface 410; and first and second parallel edges 421, 422, respectively. The counterweight support member 130 slides with first and second opposing edges 421, 422, respectively captured between the first and second opposing channels 116, 117, respectively. The first and second protuberances 411, 412, respectively, cooperate with the first and second tracks 341, 342, respectively, to cause a friction fit such that the counterweight support member 130 slides with respect to the mirror support member 110 and holds a fixed position when sliding has ceased.

Referring now to FIG. 5, illustrated is a side elevation view of the self-inspection apparatus 100 of FIG. 1 as it sits atop the toilet bowl rim 210. The toilet bowl rim 210 is captured between the mirror support member hinge portion 112 and the counterweight support member hinge portion 132. The mirror member 120 can be positioned at any suitable angle with the use of the first hinge 150, and the counterweight 140 can be positioned at a suitable similar angle with the use of the second hinge 160 to balance the mirror weight. Protuberances 411, 412 (412 not seen) cooperate with the first and second tracks 341, 342, (342 not seen) respectively, to cause a friction fit so that the mirror support member 110 does not move relative to the counterweight support member 130 when the mirror 120 is suitably positioned.

Referring now to FIG. 6, illustrated is a side elevation view of the self-inspection apparatus 100 folded for transport or storage. The mirror member 120 can be rotated inwardly and the counterweight 140 can be rotated to cover and protect the mirror 121. The mirror support member 110 can be slid toward the counterweight support member 130 for a compact package. The folded self-inspection apparatus 100 will fit conveniently in most ladies handbags.

The self-inspection apparatus 100 illustrated in FIGS. 1 thru 6 depicts but one construction of such an apparatus. Those skilled in the art understand that many modifications to the apparatus 100 of FIGS. 1 thru 6 can be made while remaining within the purview of this disclosure. Accordingly, while detail is given in many instances as to the configuration of the embodiment of the apparatus 100 of FIGS. 1 thru 6, the disclosure is not limited to such details.

Thus, a self-inspection apparatus for use with either a toilet bowl rim or a toilet seat has been described. The self-inspection apparatus is configured to readily be positioned on the rim or seat and the mirror placed at the desired angle. The counterweight is positioned so as to balance the weight of the mirror. The self-inspection apparatus is readily folded for storage and may be cleaned with common household disinfectant cleaner.

For the purposes of this discussion, use of the terms "providing" and "forming" includes: manufacture, subcontracting, purchase, etc. Those skilled in the art to which this application relates will appreciate that other and further additions, deletions, substitutions and modifications may be made to the described embodiments.

What is claimed is:

1. A self-inspection apparatus, comprising:
    a mirror support member having a first hinge proximate an end thereof, said mirror support member configured to selectively and adjustably couple to a toilet bowl rim or a toilet seat;

a mirror coupled to said mirror support member at said hinge, said mirror in combination with said hinge configured to be positionable for self-inspection; and a counterweight support member slidably coupled to the mirror support member, and further comprising a counterweight coupled to said counterweight support member proximate a second hinge, said counterweight and said mirror being substantially equal in weight.

2. The self-inspection apparatus as recited in claim 1 wherein said mirror support member has opposing channels thereon, said counterweight support member slidably coupled to the mirror support member between said opposing channels.

3. The self-inspection apparatus as recited in claim 2 wherein said end is a first end and said mirror is hingedly coupled proximate said first end and wherein said mirror support member has an opposite end having a void therein, said void configured to permit a portion of said counterweight support member to slidably travel along said void toward said first end as said counterweight support member slides between said opposing channels.

4. The self-inspection apparatus as recited in claim 1 wherein said second hinge is a friction hinge.

5. The self-inspection apparatus as recited in claim 1 wherein said mirror support member has a face on an upper surface thereof and a track on said face, and wherein said counterweight support member has an opposing face on an undersurface thereof and a protuberance on said opposing face, said protuberance configured to cause a friction fit with said track.

6. The self-inspection apparatus as recited in claim 1 further comprising a mirror support member hinge portion extending substantially normal to said mirror support member at said end and wherein a portion of said hinge is at an end of said mirror support member hinge portion.

7. A method of manufacturing a self-inspection apparatus, comprising:
   providing a mirror support member having a first hinge proximate an end thereof and configured to selectively and adjustably couple to a toilet bowl rim or a toilet seat;
   coupling a mirror to said mirror support member at said hinge;
   slidably coupling a counterweight support member to the mirror support member; and
   coupling a counterweight to said counterweight support member proximate a second hinge, wherein the counterweight and the mirror are substantially equal in weight.

8. The method as recited in claim 7 wherein providing a mirror support member includes providing a mirror support member having opposing channels said counterweight support member slidably coupled to the mirror support member between said opposing channels.

9. The method as recited in claim 8 wherein providing a mirror support member includes providing a mirror support member wherein said end is a first end, and said mirror is hingedly coupled proximate said first end and wherein said mirror support member has an opposite end having a void therein, and further including configuring said void to permit a portion of said counterweight support member to slidably travel along said void toward said first end as said secondary support member slides between said opposing channels.

10. The method as recited in claim 7 wherein said end is proximate said mirror member and further comprising forming a secondary support member hinge portion extending substantially normal to said counterweight support member proximate a second end opposite said mirror member, and wherein said second hinge is proximate said second end.

11. The method as recited in claim 7 wherein said mirror support member has a face on an upper surface thereof and a track on said face, and wherein said counterweight support member has an opposing face on an undersurface thereof and a protuberance on said opposing face, and further comprising configuring said protuberance to cause a friction fit with said track.

12. The method as recited in claim 7 further comprising forming a mirror support member hinge portion extending substantially normal to said mirror support member at said end and wherein a portion of said hinge is at an end of said mirror support member hinge portion.

13. A self-inspection apparatus, comprising:
   a mirror support member having a hinge proximate an end thereof;
   a mirror coupled to said mirror support member at said hinge; and
   a counterweight support member having a counterweight coupled thereto to said mirror support member, said mirror support member and counterweight support member slidably coupled to one another to grip a toilet bowl rim or a toilet seat, said mirror in combination with said hinge configured to be positionable for self-inspection, wherein the counterweight and the mirror are substantially equal in weight.

14. The self-inspection apparatus as recited in claim 13, wherein said mirror support member has opposing channels, and further wherein said counterweight support members slides toward or away from said end and between said opposing channels.

15. The self-inspection apparatus as recited in claim 14 wherein said end is a first end and said mirror is hingedly coupled proximate said first end and wherein said mirror support member has an opposite end having a void therein, said void configured to permit a portion of said counterweight support member to slidably travel along said void toward said first end as said counterweight support member slides between said opposing channels.

* * * * *